United States Patent [19]

Fahrenholtz et al.

[11] 4,438,207

[45] Mar. 20, 1984

[54] RADIOIMMUNOASSAY FOR CANNABINOIDS

[75] Inventors: Kenneth E. Fahrenholtz, Bloomfield; John E. Heveran, Fairfield, both of N.J.

[73] Assignee: Hoffmann-La Roche Inc., Nutley, N.J.

[21] Appl. No.: 254,022

[22] Filed: Apr. 13, 1981

Related U.S. Application Data

[63] Continuation-in-part of Ser. No. 79,125, Sep. 26, 1979, abandoned.

[51] Int. Cl.$^3$ .................. G01N 33/54; C07G 7/00; C07D 311/78
[52] U.S. Cl. ........................... 436/543; 436/544; 436/545; 436/542; 436/804; 436/815; 436/808; 436/547; 422/61; 260/112 B; 549/390
[58] Field of Search .................. 260/112 B, 345.3; 422/61; 424/1, 12; 23/230 B, 910; 252/408; 436/543, 544, 545, 808, 815, 547

[56] References Cited

U.S. PATENT DOCUMENTS

| | | | |
|---|---|---|---|
| 3,656,906 | 4/1972 | Bullock | 260/345.3 |
| 3,728,360 | 4/1973 | Pars et al. | 260/345.3 |
| 4,205,952 | 6/1980 | Cais | 23/910 |
| 4,207,307 | 6/1980 | Kaul et al. | 424/1 |
| 4,235,864 | 11/1980 | Kaul et al. | 424/1 |

FOREIGN PATENT DOCUMENTS 651653 4/1951 United Kingdom ............. 260/345.3

OTHER PUBLICATIONS

O'Connor et al., Clin. Chem., 27(6), 1104 (1981).
Eleisher et al., J. Endocrinol., 59(2), xxvii–xxviii.
Rodgers et al., Clin. Chem., 24(1), 95–100 (1978).
Teale et al., Lancet, Sep. 7, 1974, pp. 553–555.
Williams et al., J. Pharm. Pharmacol. 1980, 32: 445–448.

*Primary Examiner*—Christine M. Nucker
*Attorney, Agent, or Firm*—Jon S. Saxe; Bernard S. Leon; Alan R. Stempel

[57] ABSTRACT

An improved immunoassay for detecting cannabinoids is described. This immunoassay is characterized by utilizing, as reagents, antibody, $^{125}$I-radiolabeled antigen, an unlabeled antigen and an anion exchange resin for separation of labeled and unlabeled antigen. The iodinated tetrahydrocannabinol moiety is stabilized by the addition of small quantities of antioxidants such as butylated hydroxy toluene.

15 Claims, 2 Drawing Figures

RADIOIMMUNOASSAY FOR CANNABINOIDS

RELATED APPLICATIONS

This application is a continuation-in-part of United States patent application Ser. No. 079,125, filed Sept. 26, 1979, now abandoned.

BACKGROUND OF THE INVENTION

1. Field of the Invention

This invention relates to an improved radioimmunoassay for detecting cannabinoids. More particularly, this invention is directed to novel $^{125}$I-labeled THC derivatives, novel compounds yielding antibody, the use of said THC derivatives in the radioimmunoassay for THC and the use of an anion exchange resin for the separation of bound from unbound antigen.

2. Description of the Prior Art

For the past several years, there has been an increasing demand for qualitative and quantitative assays for identifying and measuring the constituents of marijuana in the human body. The demand for these tests is due to the need to better understand the pharmacology of this drug and to determine the presence of cannabinoids in the biological fluids of suspected abusers.

Initial attempts to determine the presence of marijuana lacked sufficient sensitivity because the primary, active constituent, Δ-9-tetrahydrocannabinol, is distributed and metabolized. Experiments with humans showed that, following almost complete metabolism, the metabolites were excreted, mainly via feces. Only small quantities of the hydroxy metabolite were noted in the urine.

The analytical methods presently available for the determination of cannabinoids in biological fluids include chromatographic, spectrometric and immunologic techniques. All of the methods are of value, especially when one method is used to cross-check the results of another technique. However, each of these types of techniques have certain drawbacks.

The gas and the liquid chromatographic methods require pre-treatment and/or purification to remove the cannabinoids from endogenous substances in the specimen which might interfere in the assay. The mass spectroscopic technique, in conjunction with gas chromatography (GC-MS), also requires sample pre-treatment. In addition, because of the size, cost and complexity of GC-MS, it is not ideal for application to routine screening.

With respect to the radioimmunoassay, the highly-lipophilic nature of the cannabinoid molecule can cause difficulties in the system in which the radioimmunoassay is performed. The cannabinoid may adhere to the glass or plastic container or the available protein in preference to remaining dissolved in the aqueous medium. Consequently, the separation of the bound from the free radiosotopically-labeled tetrahydrocannabinol derivative, which separation is the basis for the subsequent dose response measurement, can only be accomplished by judicious selection of test conditions.

To date, the radioimmunoassays for tetrahydrocannabinol have primarily employed tritiated tetrahydrocannabinol moieties for radioactive detection and charcoal or dextran-coated charcoal for separation of the bound from free antigen. For example, J. D. Teale et al., J. Pharm. Pharmac. 27, p. 465 (1975), S. J. Gross et al., Nature 252, p. 581 (1974) and Clarence E. Cook et al., NID Research Monograph 7, p. 15 (1976) all disclose the use of tritiated tetrahydrocannabinol moieties and charcoal and/or dextran-coated charcoal for the separation of bound from free antigen. In a paper presented at the 173rd National ACS Meeting, New Orleans, March 20-25, 1977, C. E. Cook presented a paper entitled "Radioimmunoassays of Cannabinoid Compounds" in which the use of tritiated and $^{125}$I-labeled tetrahydrocannabinol derivatives were used to develop radioimmunoassay procedures. Upon further investigation of the contents of this paper, it was found that the $^{125}$I-labeled tetrahydrocannabinol derivatives utilized had the following chemical structure:

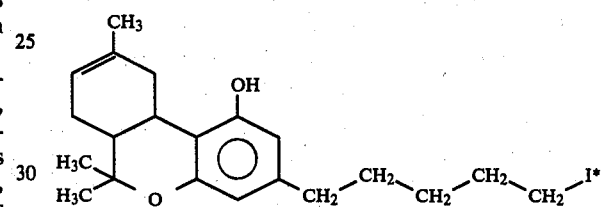

The foregoing moiety was derived from the reaction of a "cold" (i.e., nonradioactive) iodinated compound with radioactive NaI* to effect a substitution of the radioactive iodine for the "cold" iodine according to the following reaction:

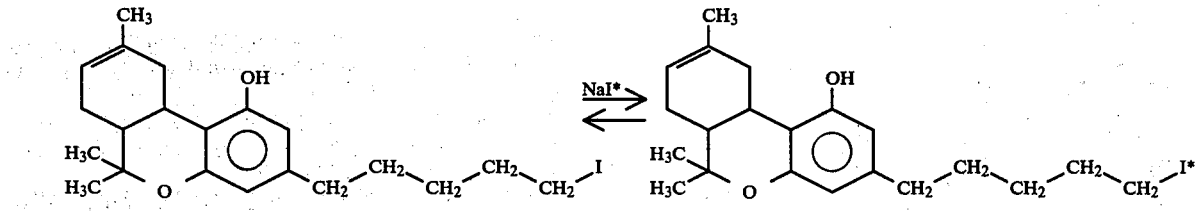

Once again, charcoal was used to separate the bound from free antigen.

In accordance with the present invention, a radioimmunoassay for tetrahydrocannabinol is disclosed wherein $^{125}$I-labeled tetrahydrocannabinol and novel $^{125}$I-labeled tetrahydrocannabinol antigens are mixed with fixed amounts of the specimen to be assayed followed by separation of bound from unbound antigen by use of an anion exchange resin.

The direct reaction of the foregoing radioactive antigens with antibody, followed by separation of bound from unbound antigen with an anion exchange resin, allows for a considerable reduction in the time necessary to run the assay without sacrificing the sensitivity of the test. For example, when operating according to the method of the claimed invention, the entire assay can be run in less than one hour as compared with the five hours which have been necessary in the prior art. Additionally, whereas prior art disclosures have required careful control of temperature at about 5° C., there is no such requirement in the practice of the present invention.

SUMMARY OF THE INVENTION

A method for the assay of tetrahydrocannabinol in a sample which method comprises mixing said sample with fixed amounts of a $^{125}$I-labeled tetrahydrocannabinol derivative and an antibody which will selectively complex with tetrahydrocannabinol, said antibody being elicited in the blood of a host animal by immunization with an immunogen separating antibody bound antigen from free antigen by means of an anion exchange resin and then measuring the radioactivity of either the free or bound antigen and comparing said value to values obtained previously with samples containing known amounts of tetrahydrocannabinol.

BRIEF DESCRIPTION OF THE DRAWINGS

FIG. I is a sample response curve for tetrahydrocannabinol radioimmunoassay using dextran-coated charcoal.

FIG. II is a sample response curve for tetrahydrocannabinol radioimmunoassay using an anion exchange resin.

DETAILED DESCRIPTION OF THE INVENTION

Figure 1:
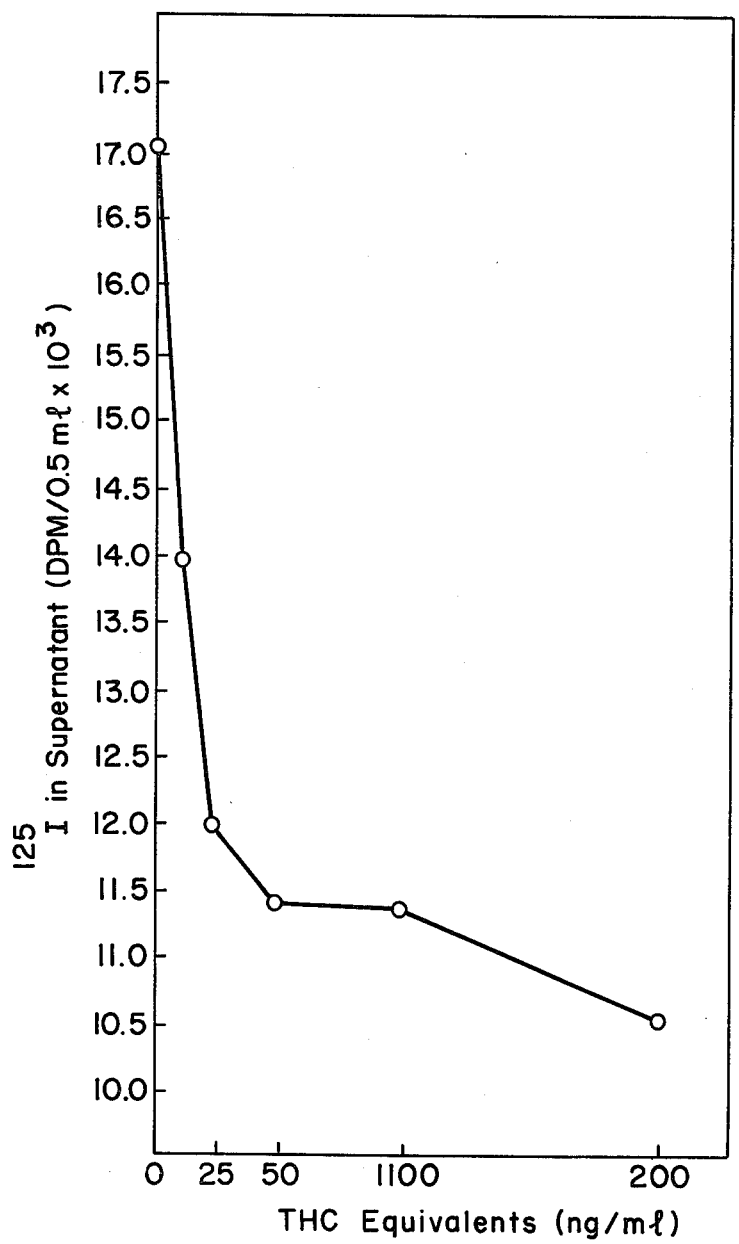

The radiolabeled antigens which can be used in the method of this invention fall into two broad categories; one category being $\Delta^8$ or $\Delta^9$ tetrahydrocannabinol with radioactive iodine attached directly to the aromatic nucleus as exemplified by formula I and the other category being a $\Delta^8$ or $\Delta^9$ tetrahydrocannabinol derivative wherein the radioactive iodine is attached to an aromatic nucleus at the end of a chain which is attached to the THC moiety by means of a connecting group as exemplified by formula II:

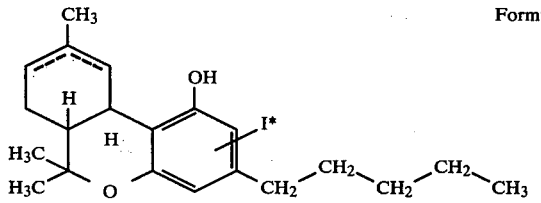

Formula I

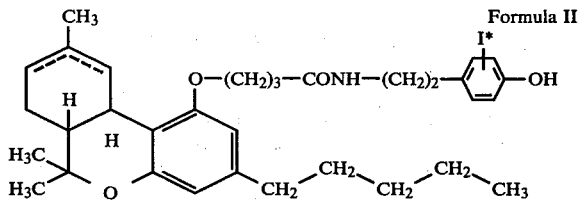

Formula II

In order to prepare the immunogen needed in the present invention, it is necessary that a haptenic compound be covalently bonded to a conventional immunogenic carrier material. As used herein, the term "immunogenic carrier material" is meant to include those materials which have the property of independently eliciting an immunogenic response in a host animal and which can be covalently coupled to the above-described hapten. Suitable carrier materials include, for example, proteins; natural or synthetic polymeric compounds such as polypeptides, e.g., polylysine or copolymers of other amino acids; polysaccharides, and the like. Particularly-preferred carrier materials are proteins and polypeptides, especially proteins.

The identity of the protein material utilized in the preparation of an immunogen of the instant invention is not critical. Examples of suitable proteins useful in the practice of this invention include mammalian serum proteins such as, for example, human gamma globulin, human serum albumen, bovine serum albumen, methylated bovine serum albumen, rabbit serum albumen and bovine gamma globulin. Other protein products will be suggested to one skilled in the art. It is generally preferred, but not necessary, that proteins be utilized which are foreign to the animal hosts in which the resulting antigen will be employed.

The immunogens of the present invention may be utilized to induce formation of antibodies specific to tetrahydrocannabinol thereof in host animals by injecting the immunogen in such a host, preferably using a conventional adjuvant. Improved titers can be obtained by repeated injections over a period of time. Suitable host animals for this purpose include mammals such as rabbits, horses, goats, guinea pigs, rats, cows, sheep, etc. The resulting antisera will contain antibodies which will selectively complex with tetrahydrocannabinol as described above.

The haptenic compounds which, when covalently linked to a carrier material, elicit antibodies in the blood of a host animal are represented by the following formula:

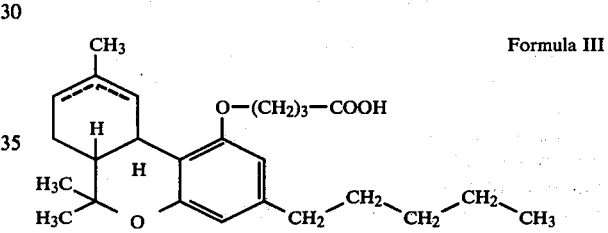

Formula III

The broken lines in the cyclohexene ring of formulas I, II and III indicate that unsaturation may be in the $\Delta^8$ or $\Delta^9$ position. The "I*" being attached at the side of the ring in formula II, rather than at a discreet point, is intended to show that the "I*" may be attached at any of the positions which are available.

The designation "$\overline{H}$" is intended to represent a stereochemical configuration where the hydrogen atom is below the plane.

The designation "I*" is intended to represent radioactive iodine.

The radioimmunoassay for tetrahydrocannabinol is based on the competitive binding to antibody with $^{125}$I-radiolabeled antigen (a tetrahydrocannabinol derivative) and unlabeled antigen, in relation to their concentrations in the solution. A number of metabolites are found in the urine following oral administration of tetrahydrocannabinol. Since the number and proportion of these metabolites vary among individuals, the results are expressed in terms of equivalents of the unlabeled standard, tetrahydrocannabinol, per ml antigen. Antigen present in a patient sample competes with labeled antigen for the limited antibody present. An unknown specimen is mixed in a test tube with fixed amounts of tetrahydrocannabinol antibody and radiolabeled antigen. After separation and centrifugation of the free antigen, an aliquot of the supernatant fluid, which contains the antigen-antibody complex, is counted in a gamma oscintillation counter. A positive specimen is identified qualitatively when the radioactivity is equal to or less than that of the positive control. A specimen can quantitatively be identified as positive by comparison to a response curve.

The preferred radiolabeled antigen for use in the radioimmunoassay of the present invention is the tetrahydrocannabinol derivative exemplified by formula II.

The iodinated tetrahydrocannabinol moiety is stabilized by the addition of small quantities of an antioxidant. Among the antioxidants which can be used for stabilization are butylated hydroxy toluene and ascorbic acid, with butylated hydroxy toluene being particularly preferred.

The resin to be used in the method of the instant invention may be those ion exchange resins, most preferably the anion type, which will interact with a net charged compound or complex. Some examples of suitable anion exchange resins are indicated in Table I.

The preferred resin is the AG 1 type.

The reagents for the disclosed radioimmunoassay are conveniently packaged in a kit. Each radioimmunoassay kit for tetrahydrocannabinol may contain:

Tetrahydrocannabinol Antibody: one vial containing 20–500 ml of tetrahydrocannabinol antiserum (rabbit) diluted in 0.01 M phosphate buffered saline with 0.1% sodium azide, as preservative, 0.2% bovine gamma globulin and 0.1% Triton X-405. Each tube requires 0.2 ml of reagent, and 500 ml of reagent would be sufficient for 2500 tubes. The preferred quantities of reagent are 100–500 ml. Most preferred is 500 ml.

$^{125}$I-Tetrahydrocannabinol Derivative: one vial containing 20–500 ml of $^{125}$I-tetrahydrocannabinol derivative (125 microcuries) in 0.01 M phosphate buffered saline containing 25% ethanol with 0.1% sodium azide and 0.003 to 0.007% butylated hydroxy toluene as preservative (sufficient for 2500 test tubes; 0.2 ml of reagent required for each tube). Preferred quantities are 100–500 ml. Most preferred is 500 ml;

Tetrahydrocannabinol Positive Urine Control: one vial containing 20–100 ml of tetrahydrocannabinol positive urine control (50–200 ng tetrahydrocannabinol/ml in normal human urine) with 0.1% sodium azide as preservative. Preferred quantities are 50–100 ml. Most preferred is 100 ml;

Normal Human Urine Control (Tetrahydrocannabinol-Free): one vial containing 20–100 ml of normal human urine with 0.1% sodium azide as preservative. Preferred quantities are 50–100 ml. Most preferred is 100 ml;

Separating Resin Reagent: one vial containing 200–1250 ml of separating resin reagent suspended in 0.1 M Tris buffer. Preferred quantities are 500–1250 ml. Most preferred is 1250 ml.

Reagents and controls should be stored at 2°–8° C. Care should be taken to avoid freezing. Reagents should not be used if they are discolored or contain particulate matter. Urine specimens which cannot be analyzed within 8 hours after voiding should be refrigerated.

Fresh urine specimens do not require any special handling or pretreatment, but an effort should be made to keep pipetted samples free of gross debris.

No additive or preservative is required for urine samples.

Additionally necessary for the radioimmunoassay are the following:

10×75 mm or 12×75 mm disposable glass test tubes.

100, 200 and 500 microliter pipets, minimum accuracy ±1%, with appropriate tips.

Vortex-type mixer.

Centrifuge of any type which generates:
1200 to 2500×g, using a swinging bucket rotor, or 3500 to 4000×g, using a fixed angle rotor.

Gamma scintillation counter for $^{125}$I. This assay was designed for use with a counter having at least 40% efficiency for $^{125}$I. However, equivalent results can be obtained with a less efficient counter by extending the counting time.

Ambient temperature is recommended throughout this procedure, however, temperature control is not critical at any step.

The qualitative test proceeds as follows after all reagents are brought to room temperature:

1. Set up and label as many tubes as are required for the Tetrahydrocannabinol Positive Urine Control, the Normal Human Urine Control, and for assays of unknown urine specimens. It is recommended that the positive control be run in triplicate because of the importance of control values in the determination.
2. Add 100 microliters of Tetrahydrocannabinol Positive Urine Control to each of three tubes.
3. Add 100 microliters of Normal Human Urine Control to each of three tubes.
4. Add 100 microliters of each unknown urine specimen to separate numbered tubes.
5. Add 200 microliters of $^{125}$I-Tetrahydrocannabinol Derivative to each tube; mix well on a vortex-type mixer.
6. Add 200 microliters of Tetrahydrocannabinol Antiserum to each tube; mix well on vortex-type mixer.
7. Incubate tubes at room temperature for 10 minutes to one hour.
8. Add 500 microliters of suspended Resin Reagent to each tube to remove unbound antigen; mix well on vortex-type mixer.
9. Allow tubes to stand at ambient temperature for several minutes to 4 hours to complete separation. The preferred time is 10 minutes.
10. Centrifuge, if necessary, the tubes for 1–5 minutes at approximately 1200 to 2500×g in a swinging bucket rotor or at 3500 to 4000×g in a fixed angle rotor (swinging bucket rotor is preferable).
11. Withdraw 500 microliters of supernatant fluid from each tube without disturbing the resin pellet (supernatant fluid must be clear) and transfer to a gamma scintillation vial for counting. Note: Withdraw supernatant as soon as possible after centrifugation.
12. Count each tube in a gamma scintillation counter for one minute to obtain disintegrations per minute (DPM). The accuracy of the counting process may be improved by counting the samples for a longer period of time. This normally will not have a significant effect on the overall precision or accuracy of the assay.

Compare disintegrations per minute obtained from each unknown specimen with the average DPM obtained from the tetrahydrocannabinol Positive Urine Control.

The test is negative for the presence of tetrahydrocannabinol or its metabolites when the DPM of the unknown specimen is greater than the average DPM of the tetrahydrocannabinol Positive Urine Control.

The test is positive when the DPM of the unknown specimen is equal to or less than the average DPM of the tetrahydrocannabinol solution used as the control.

Said solution may have a concentration ranging from 10–500 ng/ml, more preferably 50 to 200 ng/ml.

If there is need for quantitation, the following modification of the qualitative method may be used to establish a response curve in place of a single positive control value:

To establish a response curve, the Normal Human Urine Control is used as the zero point on the response curve and as the diluent for preparing other control solutions. The Normal Human Urine Control supplied has been carefully screened to ensure its efficacy in the test. The use of other "normal urines", even urines known to be drug free, as negative controls or as diluents is not recommended.

The tetrahydrocannabinol Positive Urine Control contains 50–200 ng/ml of tetrahydrocannabinol. A 1:2 dilution of the 200 ng/ml control with the Normal Human Urine Control will provide a 100 ng/ml control solution. A 1:4 dilution of the 200 ng/ml standard with the Normal Human Urine Control will provide a 50 ng/ml standard solution. A 1:8 dilution of the 200 ng/ml standard with the Normal Human Urine Control will provide a 25 ng/ml standard solution. A 1:16 dilution of the 200 ng/ml standard with the Normal Human Urine Control will provide a 12.5 ng/ml standard solution.

Set up and label 18 glass test tubes for the response curve as well as enough tubes for the sample(s). To each of tubes #1, 2 and 3, add 0.1 ml of Normal Human Urine Control; to tubes #4, 5 and 6, add 0.1 ml of the 12.5 ng/ml tetrahydrocannabinol standard; to tubes #7, 8 and 9, add 0.1 ml of the 25 ng/ml tetrahydrocannabinol standard; to tubes #10, 11 and 12, add 0.1 ml of the 50 ng/ml tetrahydrocannabinol standard; to tubes #13, 14 and 15, add 0.1 ml of the 100 ng/ml tetrahydrocannabinol standard; and to tubes #16, 17 and 18, add 0.1 ml of the 200 ng/ml tetrahydrocannabinol standard. Proceed with Steps 4 through 11 of the qualitative test procedure.

Set up a response curve as follows: Let the Y (vertical) axis indicate DPM and the X (horizontal) axis indicate nanograms of tetrahydrocannabinol equivalents per ml. Plot the points showing the average DPM of the three tubes containing each standard: 12.5 ng/ml, 25 ng/ml, 50 ng/ml, 100 ng/ml and 200 ng/ml. The DPM for 0 ng/ml (Normal Human Urine Control) is plotted at the extreme left. Fit the best line to establish the curve. (See sample response curve, FIG. II and Table VII)

Determine the tetrahydrocannabinol concentration of each urine specimen tested from the response curve. If the sample value is higher than 200 ng/ml, dilute the test specimen 1:10, 1:100 and 1:1000 with the Normal Human Urine Control, and repeat the test. If the value now falls within the response curve, multiply the ng/ml by the appropriate dilution factor to establish the concentration of tetrahydrocannabinol equivalents in the undiluted urine. If not, higher dilutions may be necessary.

A confirmatory test may be required for specimens shown to be positive. Because RIA for THC may be more sensitive than the commonly used methods, beginning the confirmatory procedure with a large volume of urine and including a concentration step will increase the likelihood of detection.

A positive and negative control should be included with each run.

Conditions specified in the procedure should not be varied.

To date, no interference due to cross-reactivity has been found to occur with the drugs enumerated in Tables II and III.

It is evident that the entire procedure, beginning with the mixture of the urine sample with labeled antigen and tetrahydrocannabinol antibody, can be completed in about 1 hour or less.

The use of an anion exchange resin for the separation of bound from unbound antigen in the methodology of the present invention provides a test having greater specificity than is achievable when dextran-coated charcoal is used to effect said separation. Table IV shows the apparent THC concentration in the urine of 80 random individuals, the assays having been carried out using dextran-coated charcoal as a means of separation. Table V shows the apparent THC concentration in the urines of 50 random individuals, the assay having been carried out using resin as a separation agent. As can be seen, the percentage of individuals showing a concentration between 10 and 15 nanograms per milliliter was only 2 percent in the case of the assay which used resin reagent as compared to 21 percent in the assay in which dextran-coated charcoal was used as a separating agent. Thus, it is clear that the methodology of the present invention produces only a negligible "baseline" or background equivalents so that it can be said, with a greater degree of certainty, that what is being detected when positive results are achieved is, in fact, the presence of THC metabolites.

Figure 2:
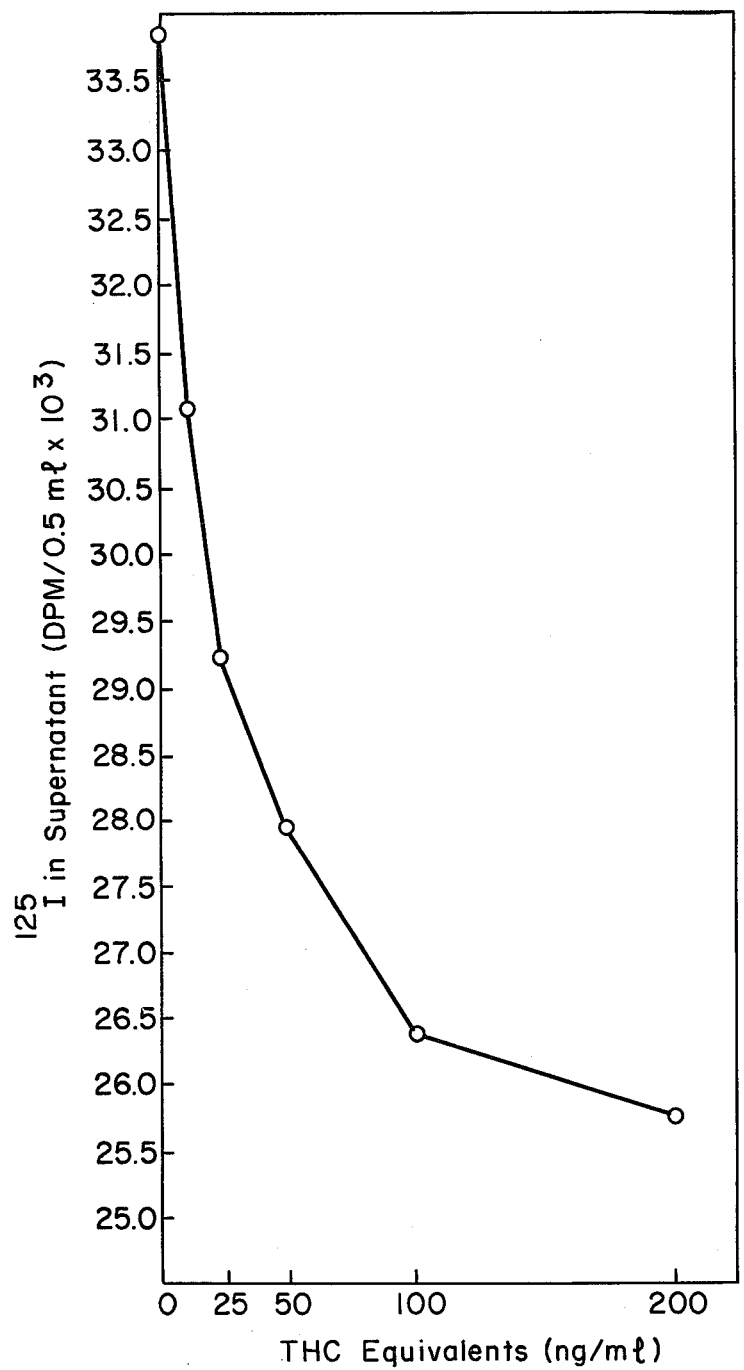

Typical response curves for resin and charcoal are shown in FIGS. 1 and 2.

The difference in DPM's observed between the charcoal and the resin system, as indicated in Tables VI and VII, may be due either to the fact that the charcoal absorbs relatively larger amounts of antibody bound antigen (in addition to free antigen) than does the resin, or that the resin binds relatively smaller amounts of free antigen than does the charcoal.

Additionally, the data in Table VIII shows the ability to determine THC levels in urine by the methodology of the present disclosure. As is indicated, urine levels of tetrahydrocannabinol can be determined as a function of time after receiving a known dosage of tetrahydrocannabinol.

DESCRIPTION OF THE PREFERRED EMBODIMENTS

Example I

Synthesis of (6aR,10aR)-4-[(6a,7,10,10a-Tetrahydro-6,6,9-trimethyl-3-pentyl-6H-dibenzo[b,d]pyran-1-yl)oxy]butanoic acid A mixture of 1.73 g (5.50 mmol) of (6aR-trans)-6a,7,10,10a-Tetrahydro-6,6,9-trimethyl-3-pentyl-6H-dibenzo[b,d]pyran-1-ol, 10 ml of dimethylsulfoxide, 3 ml of ethyl 4-bromobutyrate and 1.73 g of potassium carbonate was degassed and then heated under reflux under argon over night. The reaction was cooled, diluted with 250 ml of water and extracted with ether. The extracts were passed over a column of silica gel, and the fractions containing the intermediate ester were combined and concentrated under vacuum. The residue was dissolved in 100 ml of methanol, the solution was heated to boiling and 20 ml of water, followed by 2.2 g of sodium carbonate, was added. The mixture was heated under reflux for 3 hrs. The methanol was evaporated under vacuum, and the aqueous residue was acidified with hydrochloric acid and extracted with dichloromethane. The extracts were concentrated, and the residue was dissolved in hexane and adsorbed onto silica gel. Elution with 15% ethyl acetate in benzene, followed by evaporation, gave 1.70 g (77%) of (6aR-trans)-4-[(6a,7,10,10a-Tetrahydro-6,6,9-trimethyl-3-pentyl-6H-dibenzo[b,d]pyran-1-yl)oxy]butanoic acid as a colorless oil: ir (CHCl$_3$) 1710 cm$^{-1}$; uv max (C$_2$H$_5$OH) 225 nm (infl) ($\epsilon$17,830), 274 (1090), and 282 (1120); nmr (CDCl$_3$) $\delta$11.3 (br, CO$_2$H), 6.20 and 6.20 (two sharp d, H-2 and H-4), 5.41 (m, H-8), 4.01 (t, OCH$_2$C), 3.18 (m, H-10a), 2.59 (t, ArCH$_2$C), 2.48 (t, CCH$_2$CO), 1.69 (s, 9-CH$_3$), 1.34 and 1.06 (two s, 6,6-diCH$_3$), and 0.87 (t, $\omega$-CH$_3$); mass mol wt 400; $[\alpha]_D^{25} -195.3°$ (c 1.104, CHCl$_3$).

Anal. Calcd. for C$_{25}$H$_{36}$O$_4$: C, 74.96; H, 9.06. Found: C, 75.34; H, 8.83.

Example II

Synthesis of
(6aR, 10aR)-4-[(6a,7,10,10a-Tetrahydro-6,6,9-trimethyl-3-pentyl-6H-dibenzo[b,d]pyran-1-yl)oxy]-N-[2-(4-hydroxyphenyl)ethyl-butanamide To a solution of 2.10 g (5.24 mmol) of (6aR-trans)-4-[(6a,7,10,10a-Tetrahydro-6,6,9-trimethyl-3-pentyl-6H-dibenzo[b,d]pyran-1-yl)oxy]butanoic acid in 6 ml of benzene was added 2.1 ml (3.06 g, 24 mmol) of oxalyl chloride. When the spontaneous bubbling ceased, the mixture was heated with an 85° oil bath for 30 min. The excess oxalyl chloride and the benzene were evaporated under vacuum, 2×2 ml of benzene was added, and this was also evaporated. The residue was dissolved in 2 ml of ether and added with stirring to an ice cold solution of 0.93 g (6.78 mmol) of tyramine in 6.8 ml of 1 N sodium hydroxide, while also adding, at the same rate, 5.3 ml of ice cold 1 N sodium hydroxide. The resulting thick suspension was stirred at ice temperature for one hour, acidified with hydrochloric acid and extracted with ether. The extracts were dried and concentrated. The residue was subjected to chromatography over silica gel. Elution with 2% methanol in chloroform and concentration of the fractions containing product gave 738 mg (27%) of (6aR-trans)-4-[(6a,7,10,10a-Tetrahydro-6,6,9-trimethyl-3-pentyl-6Hdibenzo[b,d]pyran-1-yl)oxy]-N-[2-(4-hydroxyphenyl)ethyl]-butanamide as a pale yellow gum occluding 0.5 mol of water: ir (CHCl$_3$) 1665 cm$^{-1}$; uv max (C$_2$H$_5$OH) 225 (infl) ($\epsilon$20,400), 280 (3030), and 305 (infl) (830); nmr (CDCl$_3$) 6.47 and 6.73 (two d, 1,4-disubstituted benzene), 6.31 and 6.21 (two sharp d, H-2 and H-4), 5.54 (m, NH), 5.42 (m, H-8), 3.94 (t, OCH$_2$C), 3.46 (t, NCH$_2$C), 3.12 (m, H-10a), 1.65 (s, 9-CH$_3$), 1.36 and 1.08 (two s, 6,6-diCH$_3$), and 0.87 (t, $\omega$-CH$_3$); mass mol wt 519; $[\alpha]_D^{25} -154.6°$ (c 1.015, CHCl$_3$).

Anal. Calcd. for C$_{33}$H$_{45}$NO$_4$·0.5H$_2$O: C, 74.96; H, 8.77; N, 2.65. Found: C, 74.91; H, 8.78; N, 2.82.

Example III

Preparation of $^{125}$I $\Delta^8$Tetrahydrocannabinol Derivative

A total of 50 $\mu$l of a solution of 1 mg of (6aR,10aR)-4-[(6a,7,10,10a-Tetrahydro-6,6,9-trimethyl-3-pentyl-6H-dibenzo[b,d]pyran-1-yl)oxy]-N-[2-(4-hydroxyphenyl)ethyl-butanamide in 1 ml of 100% alcohol was added to a vial containing 5 mCi of Na$^{125}$I having a radioactive concentration of >100 mCi/ml. To this mixture was then added a total of 40 $\mu$l of chloramine T solution (5 mg/ml in 75% EtOH; 25% Borate buffer 0.1 M, pH 8.4). The reaction mixture was mixed for 180 seconds. After mixing, a total of 40 $\mu$l of a 1% solution of sodium meta bisulfite (75% EtOH, 25% Tris buffer 0.1 M, pH 7.0) was added to the reaction vial, and the vial contents were mixed for 30 seconds to stop the reaction.

The mixture was removed from the vial and placed on the surface of a Bio-Gel P-2 column (1.5×40 cm, 100-200 mesh) until completely absorbed on the column bed. Approximately 200 ml of 60% Tris -40% EtOH were added, and 100×1-2 ml fractions were collected. The eluate contained the above-captioned, labeled antigen.

Selected fractions of the above-mentioned eluate were pooled and diluted in 0.01 M phosphate buffered silane containing 25% ethanol with 0.1% sodium azide with 0.003 to 0.007% butylated hydroxytoluene.

Example IV

Synthesis of
(6aR,10aR)-4-[(6a,7,8,10a-Tetrahydro-6,6,9-trimethyl-3-pentyl-6H-dibenzo[b,d]pyran-1-yl)oxy]butanoic acid A mixture of 1.73 g (5.50 mmol) of (6aR-trans)-6a,7,8,10a-Tetrahydro-6,6,9-trimethyl-3-pentyl-6H-dibenzo[b,d]pyran-1-ol, 10 ml of dimethylsulfoxide, 3 ml of ethyl 4-bromobutyrate and 1.73 g of potassium carbonate was degassed and then heated under reflux under argon over night. The reaction was cooled, diluted with 250 ml of water and extracted with ether. The extracts were passed over a column of silica gel, and the fractions containing the intermediate ester were combined and concentrated under vacuum. The residue was dissolved in 100 ml of methanol, the solution was heated to boiling and 20 ml of water, followed by 2.2 g of sodium carbonate, was added. The mixture was heated under reflux for 3 hrs. The methanol was evaporated under vacuum, and the aqueous residue was acidified with hydrochloric acid and extracted with dichloromethane. The extracts were concentrated, and the residue was dissolved in hexane and adsorbed onto silica gel. Elution with 15% ethyl acetate in benzene, followed by evaporation, gave 1.70 g (77%) of (6aR-trans)-4-[(6a,7,8,10a-Tetrahydro-6,6,9-trimethyl-3-pentyl-6H-dibenzo[b,d]pyran-1-yl)oxy]butanoic acid as a colorless oil: ir (CHCl$_3$) 1710 cm$^{-1}$; uv max (C$_2$H$_5$OH) 225 nm (infl) ($\epsilon$17,830), 274 (1090), and 282 (1120); nmr (CDCl$_3$) $\delta$11.3 (br, CO$_2$H), 6.29 and 6.20 (two sharp d, H-2 and H-4), 5.41 (m, H-8), 4.01 (t, OCH$_2$C), 3.18 (m, H-10a), 2.59 (t, ArCH$_2$C), 2.48 (t, CCH$_2$CO), 1.69 (s, 9-CH$_3$), 1.34 and 1.06 (two s, 6,6-diCH$_3$), and 0.87 (t, $\omega$-CH$_3$); mass mol wt 400; $[\alpha]_D^{25} -195.3°$ (c 1.104, CHCl$_3$).

Anal. Calcd. for C$_{25}$H$_{36}$O$_4$: C, 74.96; H, 9.06. Found: C, 75.34, H, 8.83.

Example V

Synthesis of
(6aR,10aR)-4-[(6a7,8,10a-Tetrahydro-6,6,9-trimethyl-3-pentyl-6H-dibenzo[b,d]pyran-1-yl)oxy]-N-[2-(4-hydroxyphenyl)ethyl]butanamide To a solution of 1.00 g (2.49 mmol) of (6aR-trans)-4-[(6a,7,8,10a-Tetrahydro-6,6,9-trimethyl-3-pentyl-6H-dibenzo[b,d]pyran-1-yl)oxy]butanoic acid in 4 ml of benzene was added 1.0 ml (1.46 g, 11.4 mmol) of oxalyl chloride. When the evolution of gas ceased, the mixture was heated with an 80° oil, both for 30 min. The excess oxalyl chloride and the benzene were evaporated under vacuum, 2 ml of benzene was added, and this was also evaporated. The residue was dissolved in 2 ml of ether and add with stirring to an ice cold solution of 443 mg (3.23 mmol) of tyramine in 3.25 nl of 1 N sodium hydroxide, while also adding, at the same rate, 2.5 ml of ice cold 1 N sodium hydroxide. The resulting suspension was stirred at ice temperature for one hour, acidified with hydrochloric acid and extracted with ether. The extracts were dried and concentrated, and the residue was chromatographed on silica gel. Elution with 2% methanol in chloroform and concentration of the fractions containing product gave 330 mg (25%) of (6aR-trans)-4-[(6a,7,8,10a-Tetrahydro-6,6,9-trimethyl-3-pentyl-6H-dibenzo[b,d]pyran-1-yl)oxy]-N-[2-(4-hydroxyphenyl)ethyl]butanamide as a colorless oil.

Example VI

Preparation of $^{125}$I $\Delta^9$Tetrahydrocannabinol Derivative

A total of 50 μl of a solution of 1 ml of (6aR-trans)-N-[2-(4-hydroxyphenyl)ethyl]-4-(6a,7,8,10a-Tetrahydro-6,6,9-trimethyl-3-pentyl-6H-dibenzo[b,d]pyran-1-oxy)-butanamide in 1 ml of 100% alcohol was added to a vial containing 5 mCi of Na$^{125}$I having a radioactive concentration of >100 mCi/ml. To this mixture was then added a total of 40 μl of chloramine T solution (5 mg/ml in 75% EtOH; 25% Borate buffer 0.1 M, pH 8.4). The reaction mixture was mixed for 180 seconds. After mixing, a total of 40 μl of a 1% solution of sodium meta bisulfite (75% EtOH, 25% Tris buffer 0.1 M, pH 7.0) was added to the reaction vial, and the vial contents were mixed for 30 seconds to stop the reaction.

The mixture was removed from the vial and placed on the surface of a Bio-Gel P-2 column (1.5×40 cm, 100–200 mesh) until completely absorbed on the column bed. Approximately 200 ml of 60% Tris -40% EtOH were added, and 100×1-2 ml fractions were collected. The eluate contained the above-captioned, labeled antigen.

After selection of the appropriate fractions ($\geq 50\%$ binding), the fractions were pooled and diluted 1:50 in 0.01 M phosphate buffered saline (PBS) containing 25% ethanol with 0.1% sodium azide and 0.002-0.007% butylated hydroxy toluene (BHT) as preservatives.

The $\Delta^9$-Tetrahydrocannabinol Derivative [(6aR-trans)-N-[2-hydroxyphenyl)ethyl]-4-(6a,7,10,10a-Tetrahydro-6,6,9-trimethyl-3-pentyl-6H-dibenzo[b,d]pyran-1-oxy)butanamide] which is the preferred compound, upon iodination, reproducibly yield one major peak (between fractions #10 and #15) which exhibited binding in excess of 50% and one minor peak (between fractions #30 and #35) which showed no binding. The antigen reagent, prepared from the appropriate column fractions, retained >50% of its binding properties for at least six weeks.

Example VII

Multiple iodinations were performed on $\Delta^9$-tetrahydrocannabinol, and the radioisotopically-labeled reagent was used as the $^{125}$I-labeled antigen. The elution patterns varied considerably. In general, there were numerous small peaks in the elution patterns of most of the iodination products with the percent binding being lower than 50%. On occasion, there were two major peaks with insufficient binding (<50%) in either peak. The degree of binding of the iodinated $\Delta^9$-THC to the antiserum was not stable and declined rapidly after one week at 5° C.

Example VIII

Preparation of Immunogen
($\Delta^8$-Tetrahydrocannabinol-BSA Conjugate)

A 1.25 ml aliquot of a stock solution (1.009 g of (6aR,10aR)-4-[(6a,7,10,10a-Tetrahydro-6,6,9-trimethyl-3-pentyl-6H-dibenzo[b,d]pyran-1-yl)oxy]butanoic acid and 1.00 ml of 25% aqueous tetramethyl ammonium hydroxide diluted to 10 ml with water) was mixed with 8.75 ml of N,N-dimethyl formamide (DMF, Fisher, Lot 761531) to give a final volume of 10 ml with a concentration of 12.6 mg/ml. Two hundred fifty mg of Bovine Serum Albumin (BSA-Pentex-Miles Labs. Lot 260) was dissolved in 25.0 ml of distilled water and 2.5 ml of DMF. Five ml of the above solution was slowly added while stirring to the BSA solution. This solution became slightly turbid, and 6.3 ml of distilled water was added to decrease the turbidity. The remaining 5.0 ml of the above solution was slowly added. Turbidity developed again, and 6.0 ml of distilled water was added. The resultant total volume of the above solution was 49.8 ml. To this 49.8 ml of solution, 0.2 ml of 1-ethyl-3-(3-dimethylaminopropyl)carbodiimide HCl (EDCI; 500 mg/ml solution) was added, giving a final volume of 50.0 ml. The pH of the final solution was 8.4. A beaker with the 50.0 ml of final solution was wrapped in aluminum foil and placed on a magnetic stirrer in a cold room (5° C.) for 24 hrs. The solution was transferred to a dialysis bag (Spectrum Medical Industries Spectrapor #1) and dialyzed against 25% DMF-75% H$_2$O (5x) and against distilled water (2x) for four days in the cold room. Total volume recovered after dialysis was 51 ml. The dialyzate was tested by immunoelectrophoresis using IEP buffer (0.05 ionic strength, pH 8.6 buffer-5.4 g sodium diethyl barbiturate, 2.6 g sodium acetate.3-H$_2$O, 58.2 ml 0.1 N hydrochloric acid, 942 ml distilled water); 1% agarose (Kallestad) in IEP buffer; 0.1% bromophenol blue in IEP buffer and goat anti-BSA serum and a precipitin band indicated that the immunogen was different from BSA.

Example IX

Preparation of Immunogen
($\Delta^9$-tetrahydrocannabinol-BSA Conjugate)

A 1.25 ml aliquot of a stock solution (1.009 g of (6aR,10aR)-4-[(6a,7,8,10a-Tetrahydro-6,6,9-trimethyl-3-pentyl-6H-dibenzo[b,d]pyran-1-yl)oxy]butanoic acid and 1.00 ml of 25% aqueous tetramethyl ammonium hydroxide diluted to 10 ml with water) was mixed with 8.75 ml of N,N-dimethyl formamide (DMF, Fisher, Lot 761531) to give a final volume of 10 ml with a concentration of 12.6 mg/ml. Two hundred fifty mg of Bovine Serum Albumin (BSA-Pentex-Miles Labs. Lot 260) was dissolved in 25.0 ml of distilled water and 2.5 ml of DMF. Five ml of the above solution was slowly added while stirring to the BSA solution. This solution became slightly turbid, and 6.3 ml of distilled water was added to decrease the turbidity. The remaining 5.0 ml of the above solution was slowly added. Turbidity developed again, and 6.0 ml of distilled water was added. The resultant total volume of the above solution was 49.8 ml. To this 49.8 ml of solution, 0.2 ml of 1-ethyl-3-(3-dimethylaminopropyl)carbodiimide HCl (EDCI; 500 mg/ml solution) was added, giving a final volume of 50.0 ml. The pH of the final solution was 8.4. A beaker with the 50.0 ml of final solution was wrapped in aluminum foil and placed on a magnetic stirrer in a cold room (5° C.) for 24 hrs. The solution was transferred to a dialysis bag (Spectrum Medical Industries Spectrapor #1) and dialyzed against 25% DMF-75% $H_2O$ (5x) and against distilled water (2x) for four days in the cold room. Total volume recovered after dialysis was 51 ml. The dialyzate was tested by immunoelectrophoresis using IEP buffer (0.05 ionic strength, pH 8.6 buffer-5.4 g sodium diethyl barbiturate, 2.6 g sodium acetate.3-$H_2O$, 58.2 ml 0.1 N hydrochloric acid, 942 ml distilled water); 1% agarose (Kallestad) in IEP buffer; 0.1% bromophenol blue in IEP buffer and goat anti-BSA serum and a precipitin band indicated that the immunogen was different from BSA.

Example X

Butanedioic acid mono[(6aR,10aR)-6a,7,10,10a-tetrahydro-6,6,9-trimethyl-3-pentyl-6H-dibenzo[b,d]pyran-1-yl]ester A solution of 0.60 g (1.91 mmol) of (6aR-trans)-6a,7,10,10a-Tetrahydro-6,6,9-trimethyl-3-pentyl-6H-dibenzo[b,d]pyran-1-ol in 30 ml of tetrahydrofuran was degassed under argon, 625 mg (14.8 mmol) of a 57% sodium hydride in mineral oil dispersion was added, the mixture was degassed again and heated under reflux under argon for 2 hrs. The reaction was cooled to room temperature, and 1.35 g (13.5 mmol) of freshly-sublimed succinic anhydride was added. Fifteen min. later, the reaction was diluted with ethyl acetate, washed with 1 N hydrochloric acid and then with brine, dried and concentrated under vacuum. The residue was dissolved in ether, some insoluble solid was removed by filtration, and the filtrate was concentrated. The residue was dissolved in 2:1 ether:hexane and chromatographed over silica gel. Product containing fractions were combined and concentrated under vacuum to give 582 mg (74%) of [6aR-trans)-6a,7,10,10a-tetrahydro-6,6,9-trimethyl-3-pentyl-6H-dibenzo[b,d]pyran-1-yl]ester as a colorless oil: ir ($CHCl_3$) 1755 and 1720 cm$^{-1}$; uv max ($C_2H_5OH$) 225 nm (infl) ($\epsilon$8700), 275 (1900), and 282 (2090); nmr ($CDCl_3$) δ9.9 (br, $CO_2H$), 6.55 and 6.39 (two sharp d, H-2 and H-4), 5.42 (m, H-8), 2.80 (m, $COCH_2CH_2CO$), 2.49 (t, $ArCH_2C$), 1.67 (s, 9-$CH_3$), 1.35 and 1.08 (two s, 6,6-di$CH_3$), and 0.87 (t, ω-$CH_3$); mass mol wt 414; $[\alpha]_D^{25°} -196.7°$ (c 1.006, $CHCl_3$).

Anal. Calcd. for $C_{25}H_{34}O_5$: C, 72.44; H, 8.27. Found: C, 72.93; H, 8.48.

Example XI (6aR,10aR)-4-[(6a,7,8,10a-Tetrahydro-6,6,9-trimethyl-3-pentyl-6H-dibenzo[b,d]pyran-1-yl)oxy]butanoic acid A solution of 1.0 g (3.18 mmol) of (6aR,10aR)-6a,7,8,-10a-tetrahydro-6,6,9-trimethyl-3-pentyl-6H-dibenzo[b,d]pyran-1-ol and 2.32 ml of ethyl bromobutyrate in 10 ml of dimethylsulfoxide was degassed, 1.39 g of potassium carbonate was added, the mixture was degassed and then stirred at room temperature under argon overnight. The reaction was diluted with 250 ml of water and extracted with ether. The extracts were concentrated under vacuum, and the residue was dissolved in benzene and chromatographed over silica gel. The fractions containing the intermediate ester were combined and concentrated under vacuum. The residue was mixed with 60 ml of methanol, 12 ml of water and 1.30 g of sodium carbonate, and the mixture was heated under reflux for 3 hrs. The methanol was evaporated under vacuum, and the residue was acidified with hydrochloric acid and extracted with dichloromethane. The extracts were dried and concentrated, and the residue was dissolved in hexane and chromatographed over silica gel. Elution with from 5 through 20% ethyl acetate in benzene gave fractions containing product which were combined and concentrated to give 1.12 g (88%) of (6aR-trans)-4-[(6a,7,8,10a-Tetrahydro-6,6,9-trimethyl-3-pentyl-6H-dibenzo[b,d]pyran-1-yl)oxy]butanoic acid as a colorless oil: ir ($CHCl_3$) 1740 and 1715 cm$^{-1}$; uv max ($C_2H_5OH$) 225 nm (infl) ($\epsilon$13,000), 275 (2600), and 281 (2700); nmr ($CDCl_3$) δ9.7 (br, $CO_2H$), 6.28 and 6.22 [d, (H-2 and H-4) which includes m~6.25, H-10], 4.02 (t, $OCH_2C$), 3.16 (m, H-10a), 2.63 (t, $ArCH_2C$), 2.47 (t, $COCH_2C$), 1.63 (s, 9-$CH_3$), 1.37 and 1.04 (two s, 6,6-di$CH_3$), and 0.86 (t, ω-$CH_3$); mass mol wt 400; $[\alpha]_C^{25°} -122.6°$ (c 1.003, $CHCl_3$).

Anal. Calcd. for $C_{25}H_{36}O_4$: C, 74.96; H, 9.06. Found: C, 74.77; H, 8.84.

Example XII

Preparation of Antiserum

Rabbits were injected at one-week intervals for three weeks, after five weeks, and then again after six weeks with 1.0 ml of THC-BSA conjugate prepared as an emulsion (1:1) in Freund's complete adjuvant, into four sites (auxiliary and inguinal lymph regions). Subsequent injections were made at four-week intervals with immunogen in Freund's incomplete adjuvant. Bleedings, obtained by venipuncture from immunized rabbits, were allowed to stand at 2°–8° C. temperature until the clot had formed. The serum was decanted and stored at from −20° to 5° C.

Example XIII

Preparation of Resin

Three hundred mg/ml of 200–400 mesh chloride form separating resin AG 1×8 (Bio Rad) was added to the appropriate amount of Tris buffer (0.1 M pH 7.7). The mixture was allowed to settle, and the supernate was poured off. It was then resuspended in the appropriate amount of Tris buffer.

TABLE I

Anionic Resins

AG 1-X8, 200–400 mesh
Bio-Rex 9, 200–400 mesh
AG 1-X10, 100–200 mesh
AG 1-X2, 200–400 mesh
Sephadex-LH 60
AG 21K, 50–100 mesh
QAE-Sephadex, A-25
Bio-Gel P-2, 200–400 mesh
Bio-Beads SM-2
DEAE-Sephadex, A-25
AG 2-X8, 50–100 mesh
AG MP-1, 200–400 mesh All resins which begin with "AG" and "Bio" are manufactured by BIO-RAD Labs, 32 East Griffin Avenue, Richmond, Calif. 94804.

All resins which mention "Sephadex" are manufactured by Pharmacia Fine Chemicals, 800 Central Avenue, Piscataway, New Jersey 08851.

TABLE II

| List of Non-Interfering Drugs (In Vivo) | |
|---|---|
| aminopyrine | methyprylon |
| amphetamine | oxyphenbutazone |
| caffeine | phenobarbital |

TABLE II-continued

List of Non-Interfering Drugs (In Vivo)

| | |
|---|---|
| chlordiazepoxide HCl | promethazine |
| chloroquine | secobarbital |
| chlorpromazine | trifluoroperazine |
| glutethimide | |

Drugs tested in vivo and found not to interfere using 10 ng THC equivalents/ml as the limit value.

TABLE III

List of Non-Interfering Drugs (In Vitro)

| | |
|---|---|
| amobarbital | morphine |
| amphetamine | morphine glucormide |
| barbital-sodium | nalorphine |
| butabarbital | oxycodone HCl |
| chlorpromazine | pentobarbital |
| cocaine | phenobarbital |
| codeine phosphate | phentermine |
| dextromethorphan | poppy seed |
| meperidine HCl | proxyphene |
| methadone | secobarbital |
| methamphetamine | sodium secobarbital |
| methaqualone | |

Drugs tested in vitro and found not to interfere using a 10 ng THC equivalent/ml as the unit value.

TABLE IV

Apparent THC Concentration in the Urines of 80 Random Individuals

| Concentration (ng THC E$^a$/ml) | Number of Individuals | Percentage |
|---|---|---|
| 0 | 4 | 5.0 |
| >0 but ≦10 | 38 | 47.5 |
| >10 but ≦15 | 17 | 21.25 |
| >15 | 21 | 26.25 |

$^a$Results expressed as $\Delta^9$ tetrahydrocannabinol equivalents (E) by the $^{125}$I assay using dextran-coated charcoal as a separating agent.

TABLE V

Apparent THC Concentration in the Urines of 50 Random Individuals

| Concentration (ng THC E$^a$/ml) | Number of Individuals | Percentage |
|---|---|---|
| 0 | 32 | 64 |
| >0 but ≦10 | 13 | 26 |
| >10 but ≦15 | 1 | 2 |
| >15 | 4 | 8 |

$^a$Results expressed as $\Delta^9$ tetrahydrocannabinol equivalents (E) by the $^{125}$I assay using resin reagent as a means of separation.

TABLE VI

THC Concentration vs. Response

| ng/ml THC | DPM$^a$ |
|---|---|
| 0 | 17108 |
| 12.5 | 13946 |
| 25.0 | 11964 |
| 50.0 | 11389 |
| 100.0 | 11342 |
| 200.0 | 10474 |

$^a$By the $^{125}$I RIA using dextran-coated charcoal to separate bound from free antigen.

TABLE VII

THC Concentration vs. Response

| ng/ml THC | DPM$^a$ |
|---|---|
| 0 | 33836 |
| 12.5 | 31096 |
| 25 | 29212 |
| 50 | 27945 |
| 100 | 26333 |
| 200 | 25651 |

$^a$By the $^{125}$I RIA using the resin reagent to separate bound from free antigen.

TABLE VIII

Urine THC Levels as a Function of Time After Receiving Known Dosages of Selected Cannabinoids Tetrahydrocannabinol Concentration, ng THC E/ml$^a$

| | THC$^b$ 2.5 mg | | | |
|---|---|---|---|---|
| Time, h | 1$^d$ | 1$^{c,d}$ | 2 | 2$^c$ |
| 0 | 28.0 | 10.0 | 5.0 | 5.0 |
| 0–4 | 45.0 | 29.0 | 4.0 | 11.0 |
| 4–8 | 37.5 | 70.0 | 26.0 | 13.5 |
| 8–12 | — | — | 10.0 | 7.5 |
| 12–24 | 45.0 | 72.5 | 7.5 | 17.5 |
| 24–48 | 20.0 | 41.5 | 22.5 | 7.5 |
| 48–72 | 27.5 | 40.0 | 12.5 | 5.0 |

$^a$Nanograms of $\Delta^9$ THC equivalents per ml of urine.
$^b$Subjects smoked cigarettes prepared to deliver 2.5 mg of a given cannabinoid assuming 50% delivery.
$^c$Sodium azide was added to an aliquot of each urine specimen to give a concentration of 10 mg %.
$^d$Subject #1 was found to have smoked marijuana prior to the study.

What is claimed is:

1. (6aR,10aR)-4-[(6a,7,10,10a-tetrahydro-6,6,9-trimethyl-3-pentyl-6H-dibenzo[b,d]pyran-1-yl)oxy]-N-[2-(4-hydroxyphenyl)ethyl]-butanamide.

2. $^{125}$I-(6aR,10aR)-4-[(6a,7,10,10a-tetrahydro-6,6,9-trimethyl-3-pentyl-6H-dibenzo[b,d]pyran-1-yl)oxy]-N-[2-(4-hydroxyphenyl)ethyl]-butanamide.

3. (6aR,10aR)-4-[(6a,7,8,10a-tetrahydro-6,6,9-trimethyl-3-pentyl-6H-dibenzo[b,d]pyran-1-yl)oxy]-N-[2-(4-hydroxyphenyl)ethyl]-butanamide.

4. $^{125}$I-(6aR,10aR)-4-[(6a,7,8,10a-tetrahydro-6,6,9-trimethyl-3-pentyl-6H-dibenzo[b,d]pyran-1-yl)oxy]-N-[2-(4-hydroxyphenyl)ethyl]-butanamide.

5. An immunogen comprising bovine serum albumen and (6aR,10aR)-4-[(6a,7,10,10a-tetrahydro-6,6,9-trimethyl-3-pentyl-6H-dibenzo[b,d]pyran-1-yl)oxy]-butanoic acid.

6. An immunogenic compound derived from the reaction of (6aR,10aR)-4-(6a,7,8,10a-tetrahydro-6,6,9-trimethyl-3-pentyl-6H-dibenzo[b,d]pyran-1-yl)oxy]-butanoic acid and bovine serum albumen.

7. A method for the production of antibody useful for the assay of tetrahydrocannabinol, which comprises eliciting said antibody in the blood of a host animal by immunization with an immunogenic compound derived from the reaction of (6aR,10aR)-4-(6a,7,8,10a-tetrahydro-6,69-trimethyl-3-pentyl-6H-dibenzo[b,d]pyran-1-yl)oxy]butanoic acid and bovine serum albumen.

8. A method for the assay of tetrahydrocannabinol in a sample which method comprises mixing said sample with fixed amounts of an $^{125}$I-labeled tetrahydrocannabinol derivative selected from the group comprising $^{125}$I-(6aR,10aR)-4-[(6a,7,10,10a-tetrahydro-6,6,9-trimethyl-3-pentyl-6H-dibenzo[b,d]-pyran-1-yl)oxy]-N-[2-(4-hydroxyphenyl)ethyl]-butanamide and $^{125}$I-(6aR,10aR)-4-[(6a,7,8,10a-tetrahydro-6,6,9-trimethyl-3-pentyl-6H-dibenzo[b,d]-pyran-1-yl)oxy]-N-[2-(4-hydroxyphenyl)ethyl]-butanamide and an antibody which will selectively complex with tetrahydrocannabinol, said antibody being elicited in the blood of a host animal by immunization with an immunogenic compound derived from the reaction of [(6aR,10aR)-4-(6a,7,8,10a-tetrahydro-6,6,9-trimethyl-3-pentyl-6H-dibenzo[b,d]pyran-1-yl)oxy]butanoic acid and bovine serum albumen, separating antibody bound tetrahydrocannabinol and $^{125}$I-labeled derivative (collectively called "antigen") from free antigen by means of an anion exchange resin and, then, measuring the radioactivity of either the free or bound antigen and comparing said value to values obtained previously with samples containing known amounts of tetrahydrocannabinol.

9. A test kit for the detection or assay of tetrahydrocannabinol in a sample comprising:
   a. a first container means containing a preselected amount of an $^{125}$I-labeled tetrahydrocannabinol derivative selected from the group comprising $^{125}$I-(6aR,10aR)-4-[6a,7,10,10a-tetrahydro-6,6,9-trimethyl-3-pentyl-6H-dibenzo[b,d]pyran-1-yl)oxy]-N-[2-(4-hydroxyphenyl)ethyl]butanamide and $^{125}$I-(6aR,10aR)-4-[(6a,7,8,10a-tetrahydro-6,6,9-trimethyl-3-pentyl-6H-dibenzo[b,d]pyran-1-yl)oxy]-N-[2-(4-hydroxyphenyl)ethyl]butanamide;
   b. a second container means containing a preselected amount of an antibody reagent which will selectively complex with both tetrahydrocannabinol and said $^{125}$I-labeled derivative (collectively called "antigen") said antibody being elicited in the blood of a host animal by immunization with an immunogenic compound derived from the reaction of [(6aR,10aR)-4-(6a,7,8,10a-tetrahydro-6,6,9-trimethyl-3-pentyl-6H-dibenzo[b,d]pyran-1-yl)oxy]butanoic acid and bovine serum albumen; and,
   c. a third container means containing a preselected amount of an anion exchange resin for separating antibody bound antigen from free antigen.

10. The test kit of claim 9, further comprising a fourth container means containing a preselected amount of a positive urine control which contains a known concentration of tetrahydrocannabinol, against which samples to be assayed can be compared.

11. The test kit of claim 10 further comprising a fifth container means containing a preselected amount of a normal urine control which is free of any tetrahydrocannabinol, for diluting said positive urine control.

12. The test kit of claim 9 wherein said $^{125}$I-tetrahydrocannabinol derivative reagent comprises a composition containing 500 ml of $^{125}$I-tetrahydrocannabinol derivative possessing radioactivity of 125 microcuries in 0.01 M phosphate buffered saline containing 25% ethanol with 0.1% sodium azide and 0.003 to 0.007% butylated hydroxy toluene.

13. The test kit of claim 9 wherein said antibody reagent comprises a composition containing 500 ml of tetrahydrocannabinol rabbit antibody diluted in 0.01 M phosphate buffered saline with 0.1% sodium azide, 0.2% bovine gamma globulin and 0.1% Triton X-405.

14. The test kit of claim 9 wherein the anion exchange resin comprises 1250 ml of AG1 resin suspended in 0.1 M Tris buffer.

15. The test kit of claim 10 wherein said sample containing known amounts of tetrahydrocannabinol comprises a composition containing 200 ng of tetrahydrocannabinol in 100 ml normal human urine and 0.1% sodium azide.

* * * * *